(12) United States Patent
Chodorow et al.

(10) Patent No.: US 10,624,779 B2
(45) Date of Patent: Apr. 21, 2020

(54) BRUXISM TREATMENT DEVICE (71) Applicant: Sacks Holdings, Inc., Solana Beach, CA (US)

(72) Inventors: Devin S. Chodorow, Rancho Santa Fe, CA (US); Ingram S. Chodorow, Rancho Santa Fe, CA (US); Christopher G. Ross, Carlsbad, CA (US); Peter M. On, Carlsbad, CA (US)

(73) Assignee: Sacks Holdings, Inc., San Diego, CA (US)

( * ) Notice: Subject to any disclaimer, the term of this patent is extended or adjusted under 35 U.S.C. 154(b) by 370 days.

(21) Appl. No.: 14/546,944

(22) Filed: Nov. 18, 2014

(65) Prior Publication Data

US 2015/0305918 A1 Oct. 29, 2015

Related U.S. Application Data

(60) Provisional application No. 61/985,985, filed on Apr. 29, 2014.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ............... A61F 2005/563; A61F 5/566; A61F 5/56–58; A63B 71/085; A63B 2071/086; A63B 23/032; A63B 9/06; A63B 2071/088; A63B 71/081; A63B 23/03; A61C 7/08; A61C 7/36; A61C 5/14; A61C 7/00; A61C 9/0006; A61C 19/063; A61M 16/049; A61M 16/0488–0495; Y10S 602/902; Y10T 29/49567; Y10T 29/49568; A62B 9/06
USPC ......... 128/861, 848, 862, 206.29; 433/6, 24, 433/37, 318, 19; 602/902; 482/11; 601/38; 606/235
See application file for complete search history.

(56) References Cited

U.S. PATENT DOCUMENTS

| 4,976,618 A | 12/1990 | Anderson |
| 5,031,611 A * | 7/1991 | Moles ................... B63C 11/186 128/201.11 |
| D373,421 S | 9/1996 | Brown |

(Continued)

FOREIGN PATENT DOCUMENTS

WO    WO 2012153066 A1 *  11/2012  ........... A63B 71/085

OTHER PUBLICATIONS

Notice of Allowance for U.S. Appl. No. 29/623,580 dated Jul. 31, 2019, 6 pages.

(Continued)

*Primary Examiner* — Keri J Nelson
*Assistant Examiner* — Michelle J Lee
(74) *Attorney, Agent, or Firm* — Kilpatrick Townsend & Stockton LLP (57) ABSTRACT

An intraoral device is disclosed. The device includes a curved portion configured to extend along a user's teeth, and first and second back portions connected to the curved portion. In addition, the device includes a plurality of projections extending from each of the first and second back portions, where the projections are positioned such that, when in the user's mouth, the projections are between upper and lower teeth of the user.

24 Claims, 5 Drawing Sheets

(56) References Cited

U.S. PATENT DOCUMENTS

| | | | |
|---|---|---|---|
| 5,584,687 A | 12/1996 | Sullivan et al. | |
| D397,442 S | 8/1998 | Kittelsen | |
| D406,405 S | 3/1999 | Yoshida | |
| 6,152,138 A * | 11/2000 | Brown | A61F 5/56 128/859 |
| 6,536,424 B2 * | 3/2003 | Fitton | A61M 16/0488 128/200.24 |
| 6,978,786 B2 | 12/2005 | Sabbagh | |
| 7,490,609 B2 | 2/2009 | Brown | |
| 8,196,587 B2 | 6/2012 | Chodorow | |
| 8,201,560 B2 * | 6/2012 | Dembro | A61F 5/566 128/861 |
| 8,701,673 B2 | 4/2014 | Chodorow | |
| 8,733,364 B2 | 5/2014 | Chodorow | |
| 10,342,694 B1 | 7/2019 | Mowell et al. | |
| 2009/0165805 A1 * | 7/2009 | Syrop | A61F 5/566 128/861 |
| 2010/0206314 A1 * | 8/2010 | Brown | A61F 5/566 128/861 |
| 2011/0004129 A1 * | 1/2011 | Wavle | A63B 21/028 601/38 |
| 2011/0139162 A1 | 6/2011 | Chodorow | |
| 2012/0283069 A1 * | 11/2012 | Martin | A63B 21/023 482/11 |
| 2014/0238419 A1 * | 8/2014 | Lovat | A63B 71/085 128/862 |
| 2015/0133269 A1 * | 5/2015 | Landis | A63B 23/032 482/11 |
| 2016/0001160 A1 * | 1/2016 | Engel | A63B 71/085 128/861 |
| 2019/0117442 A1 | 4/2019 | Chodorow | |

OTHER PUBLICATIONS

Non-Final Office Action for U.S. Appl. No. 29/623,580 dated Oct. 30, 2018, 11 pages.

* cited by examiner

BRUXISM TREATMENT DEVICE

CROSS-REFERENCES TO RELATED APPLICATIONS

This application claims the benefit of U.S. Provisional Application No. 61/985,985 entitled "BRUXISM TREATMENT DEVICE," and filed on Apr. 29, 2014, the entirety of which is hereby incorporated by reference herein.

FIELD OF THE DISCLOSURE

The present invention relates, generally, to dental protection devices, and, more particularly, to bruxism protection and treatment devices.

BACKGROUND

Bruxism is a term that refers to excessive grinding and clenching of the teeth. Those with bruxism are often unaware that they have developed this habit, and often do not know that treatment is available until damage to the mouth and teeth has been done. Each individual may experience different symptoms which may include: abraded teeth, facial pain, oversensitive teeth, tense facial and jaw muscles, headaches, dislocation of the jaw, damage to the tooth enamel, exposing the inside of the tooth (dentin), a popping or clicking in the temporomandibular joint (TMJ), tongue indentations, and/or damage to the inside of the cheek.

While the causes of bruxism are sometimes not known or not recognized, oral health specialists often point to excessive stress and certain personality types as being associated with bruxism. Bruxism often affects persons with nervous tension such as anger, pain, or frustration, and/or persons with aggressive, hurried, or overly competitive tendencies.

Bruxism may be diagnosed during dental examinations, and may, for example, be indicated by the upper surfaces of the teeth appearing flat. If symptoms are present, the condition is usually observed for changes over the next several visits before a treatment program is established.

Specific treatment for bruxism may be determined by a dentist or physician based on one or more factors, such as the person's age, overall health, medical history, severity of symptoms, patient or doctor preference, and tolerance for specific medications, procedures, or therapies.

In many cases, bruxism can be successfully treated by:
a. Behavior modification achieved through instruction from an expert regarding helping the patient learn to rest his/her tongue, teeth, and lips properly, and/or how to rest his/her tongue upward while keeping the teeth apart and lips closed to relieve discomfort on the jaw.
b. A specially-fitted plastic mouth appliance may be worn at night to absorb the force of biting. This appliance may help to prevent future damage to the teeth and aid in changing the patient's behavior.
c. Biofeedback which involves an electronic instrument that measures the amount of muscle activity of the mouth and jaw—indicating to the patient when too much muscle activity is taking place so that the behavior can be changed. This is especially helpful for daytime bruxers.

Bruxism patients may present with a variety of symptoms, including anxiety, stress, tension, depression, earache, eating disorders, insomnia, headache and/or jaw pain. Eventually, bruxing shortens and blunts the teeth being ground, and may lead to myofacial muscle pain, temporomandibular joint dysfunction and headaches. In severe, chronic cases, it can lead to arthritis of the temporomandibular joints. The jaw clenching that often accompanies bruxism can be an unconscious neuromuscular daytime activity, which should be treated as well, usually through physical therapy, such as recognition and stress response reduction.

Prior art bruxism management techniques include minimizing the abrasion of tooth surfaces by the wearing of an acrylic dental guard or splint, designed in the shape of an individual's upper or lower teeth from a bite mold. Mouth guards are obtained through visits to a dentist for measuring, fitting, and ongoing supervision. These devices use one or more of four approaches: constraint of dental movement such that serious damage to the temperomandibular joints is prevented, stabilization of occlusion by minimizing the gradual changes to the positions of the teeth that typically occur with bruxism, prevention of tooth damage, and the enabling of a bruxism practitioner to judge in broad terms the extent and patterns of bruxism, for example, through examination of physical indentations on the surface of a worn dental guard. Dental guards typically worn over an extended period during many night's sleep, may be seen in U.S. Pat. Nos. 4,976,618, 5,873,365, and 6,152,138. Another type of device sometimes given to a bruxer is a repositioning splint which may look similar to a traditional night guard, but is designed to change the occlusion or "bite" of the patient.

Bruxism is associated with a person's mandible which is connected to the cranium by the temporomandibular joints located immediately in front of the ears. Rotation of the mandible about these joints is accomplished by the masticatory muscles, each of which extends from an opposite side of the mandible to a connecting point on the cranial bones. The masticatory muscles have an at rest position between their extended and contracted states. Under normal physiological conditions involving the outgrowth of a full complement of teeth, the mandibular portion of each temporomandibular joint will rest lightly in the cranial portion of the joint, and the muscles will be relaxed or at rest.

Masticatory muscle related strain and/or pain can arise due to differences in occlusal pressures along the upper and lower dental arches. Temporomandibular joint dysfunction syndrome relates to occlusion-muscle incompatibility. Masticatory muscle accommodation is a key factor in the etiology of this syndrome. Psychological tension and stress can lead to temporomandibular joint dysfunction or bruxism in otherwise stable mouths with normal occlusion.

The most frequent jaw movement involves elevation of the mandible from its rest position into centric occlusion. Simple elevation of the mandible is normally powered almost entirely by the elevator muscles, other muscles providing only a minor bracing action. The bilateral temporals, masseters and medial pterygoids provide an excess supply of elevator motor units. Since these motor units alternate in function, with fatigued units relaxing to rest while others take their place, mandible elevation can be continued over long periods of time without over fatiguing these muscles.

Occlusion-muscle dysfunction alters this condition drastically because accommodation has a highly selective effect on the masticatory muscles, increasing their activity disproportionately in certain areas of the bilateral complex. In the presence of occlusion muscle disharmony, a traumatic closure into centric occlusion requires that the mandible be adjusted every time it is elevated into occlusion. If, for example, the required adjustment is horizontal, the muscle areas capable of producing such horizontal movements must be called into activity with the same frequency as are the elevator muscle areas. Unfortunately, there are far fewer of these horizontal-adjustor motor units than elevator motor units.

Ultimately, the functional capacity of these comparatively few horizontal motor units is exceeded, which triggers an exhaustion-in coordination-spasm sequence and development of the temporomandibular joint syndrome symptoms. The resulting tenderness and spasms are found most frequently in the lateral pterygoid muscles which function as anterior adjustors of mandibular placement.

In psychological stress related syndromes, the muscles become fatigued as a result of nocturnal clenching or grinding of the teeth. These nocturnal activities give rise to the same symptoms as malocclusion-based temporomandibular joint dysfunction.

The sequence of muscle dysfunction can spread beyond the masticatory muscles, producing a constellation of primary symptoms of the temporomandibular joint pain-dysfunction syndrome. These symptoms include pain and/or tenderness in the temporomandibular joint area or masticatory muscles; "clicking" in the temporomandibular joint; limitation of jaw opening; restriction of jaw movement; and secondary symptoms which are medical in nature, being transmitted to other, more distant areas of the head and neck. These secondary symptoms probably include some of the most widespread and problematic conditions medicine has to deal with, namely, headache (including "tension" headaches), atypical facial neuralgias, tinnitus and neck and ear pain, among others. Also, certain neuromuscular disorders of the face, head and neck, shoulders, back, arms and hands can occur. These secondary symptoms are functional disturbances which exhibit no organic changes in the affected tissues, making diagnosis difficult. They are often ill-defined and difficult for the patient to describe.

These symptoms are usually diagnosed as purely medical in nature because they occur at some distance from the teeth. Their masticatory muscle origin, unfortunately, is not readily apparent. The usual result is that treatment is mistakenly directed to the secondary symptom's locale rather than to the underlying malocclusion. Such malocclusions are common but difficult to detect. Intercuspation of the teeth appears normal, while the underlying faulty (accommodation-necessitating) craniomandibular relationship is hidden by the automatic compensatory action of the muscles. The secondary symptoms resulting from temporomandibular joint dysfunction thus are usually treated palliatively instead of having their basic cause eliminated. For malocclusion-based muscle dysfunction, definitive therapy is essentially an orthopedic procedure and requires correction of the faulty cranio-mandibular relationship by a dentist. For psychological stress-related dysfunctions, treatment may be addressed in other ways.

Some notable prior art methods of treating temporomandibular joint dysfunction and bruxism include clinical monitoring devices to measure the amount of pressure being asserted, splints to be worn during sleep to prevent the wearing of teeth, and behavior modification devices, which provide an electrical shock to the jaw muscles to interrupt nocturnal bruxing episodes without waking the patient.

BRIEF SUMMARY

One aspect of the present disclosure relates to a dental device. The dental device includes a curved portion, first and second back portions connected to the curved portion, and at least three projections extending from each of the first and second back portions. In some embodiments, each of the projections defines a centerline, and in some embodiments, the centerline of one of the at least three projections extending from each of the first and second back portions is non-coplanar with a plane extending through the centerlines of others of the at least three projections extending from each of the first and second back portions.

In some embodiments, the at least three projections can be cylindrical projections. In some embodiments, the at least three cylindrical projections can be tapered. In some embodiments, the at least three cylindrical projections are tubular. In some embodiments, at least one of the projections on each of the first and second back portions has an enlarged diameter, relative to the diameters of the others of the projections on each of the first and second back portions. In some embodiments, the at least one of the projections having the enlarged diameter is positioned relatively farther from the curved portion than the others of the projections on each of the first and second back portions.

In some embodiments, the first and second back portions are substantially planar members. In some embodiments, the first and second back portions are substantially planar in that the first and second back portions are flat when they are in an undeformed state. In some embodiments, the centerlines of the projections are perpendicular to the one of the first and second back portions with which the projections connect. In some embodiments, the first and second back portions are connected to the curved portion via a pair of beam members. In some embodiments, the beam members define an opening that can allow passage of saliva.

One aspect of the present disclosure relates to a method of minimizing tooth abrasion. The method includes inserting a dental device into a mouth. The dental device includes a curved portion, first and second back portions connected to the curved portion, and at least three projections extending from each of the first and second back portions. In some embodiments, each of the projections defines a centerline, and in some embodiments, the centerline of one of the at least three projections extending from each of the first and second back portions is non-coplanar with a plane extending through the centerlines of others of the at least three projections extending from each of the first and second back portions. In some embodiments, the method includes positioning the dental device such that the at least three projections extending from each of the first and back portions extend between upper a lower teeth.

In some embodiments of the method, the at least three projections of the dental device are cylindrical projections. In some embodiments of the method, the at least three cylindrical projections are tapered. In some embodiments of the method, the at least three cylindrical projections are tubular. In some embodiments of the method, at least one of the projections on each of the first and second back portions has an enlarged diameter. In some embodiments of the method, the at least one of the projections having the enlarged diameter is positioned relatively farther from the curved portion than the others of the projections on each of the first and second back portions.

In some embodiments of the method, the first and second back portions are substantially planar members. In some embodiments of the method, the centerlines of the projections are perpendicular to the one of the first and second back portions with which the projections connect. In some embodiments of the method, the first and second back portions are connected to the curved portion via a pair of beam members. In some embodiments of the method, the beam members define an opening that allows passage of saliva.

One aspect of the present disclosure relates to an intraoral device. The intraoral device includes a curved portion that extends along a user's teeth, first and second back portions connected to the curved portion, and a plurality of non-coplanar projections extending from each of the first and second back portions. In some embodiments, the projections are positioned such that, when in the user's mouth, the projections are between upper and lower teeth of the user.

In some embodiments, three projections extend from each of the first and second back portions. In some embodiments, the projections are substantially cylindrical, and in some embodiments, one or more of the projections is tubular. In some embodiments, one or more of first and second back portions can include one or more holes, that can be each aligned with one of the projections.

In some embodiments, the projections have differing sizes, and in one embodiment, one or more of the projections can be tapered so as to be larger proximate the first and second back portions and smaller distal the first and second back portions. In some embodiments, the first and second back portions are connected to the curved portion by a plurality of beams. In some embodiments, the dental device includes an opening between each pair of adjacent beams.

One inventive aspect is an intraoral device. The device includes a curved portion configured to extend along a user's teeth, and first and second back portions connected to the curved portion. In addition, the device includes a plurality of projections extending from each of the first and second back portions, where the projections are positioned such that, when in the user's mouth, the projections are between the upper and lower teeth of the user.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION

Embodiments of the present invention include an intraoral device to be used, for example, when a person sleeps. The device is positioned between the person's upper and lower teeth to reduce symptoms and damage caused, for example, by bruxism and temporomandibular dysfunction. It is effective, very simple to use and relatively low in cost.

For the purposes of explanation, the ensuing details are set forth in order to provide a thorough understanding of various embodiments. It will be apparent, however, to one skilled in the art that various embodiments may be practiced without some of these specific details. For example, various features may be shown as components of some specific embodiments. In other instances, previously known features may be shown without unnecessary detail in order to avoid obscuring the inventive features of the described embodiments.

Embodiments provided herein are examples only, and are not intended to limit the scope, applicability, or configuration of the disclosure. Rather, the ensuing description of the embodiments will provide those skilled in the art with an enabling description for implementing one or more embodiments. It should be understood that various changes may be made in the function and arrangement of elements without departing from the spirit and scope of the disclosed embodiments.

Figure 1:
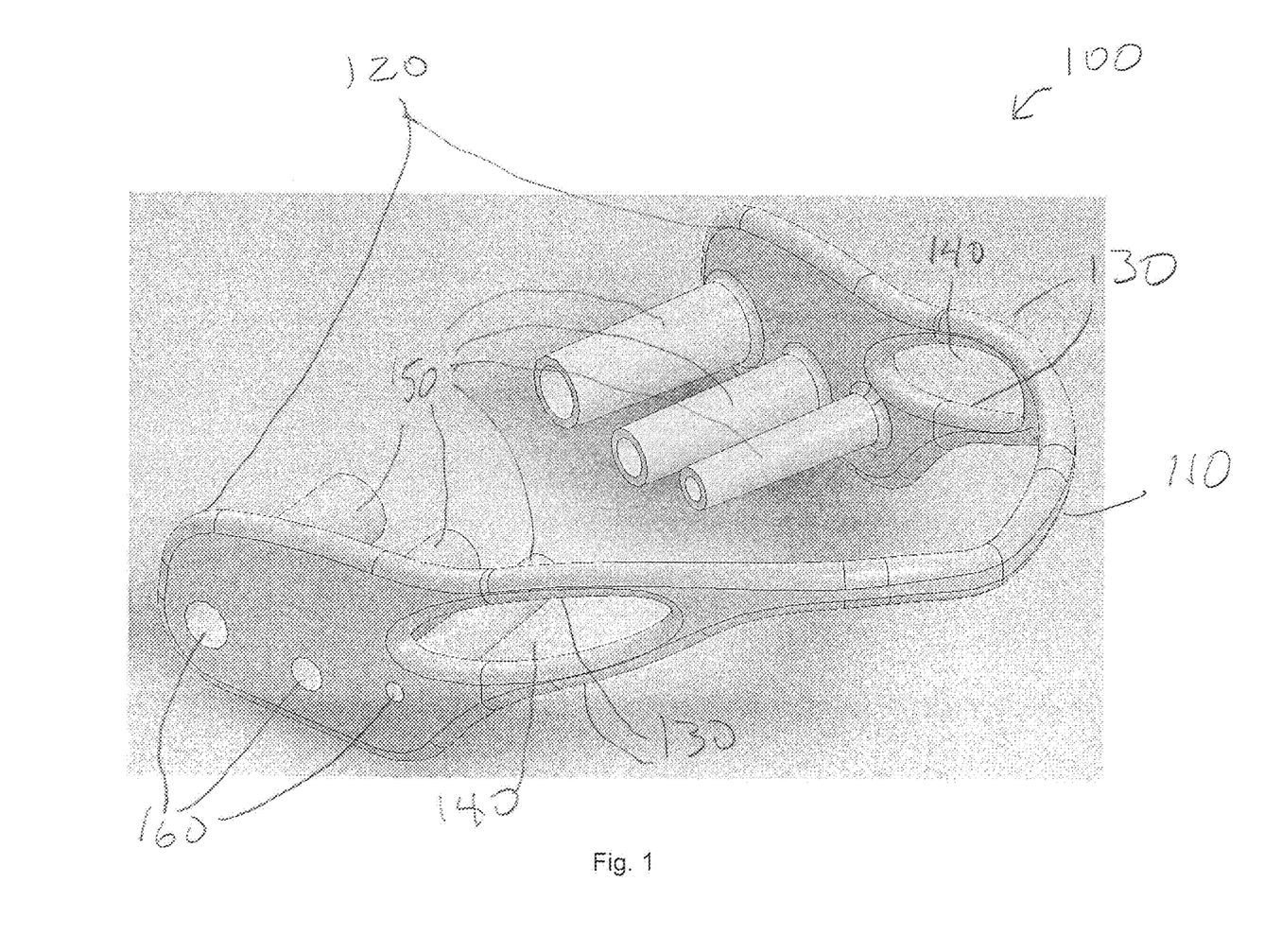
FIG. 1 is a perspective view of one embodiment of a bruxism treatment device.

FIG. 1 is a perspective view of one embodiment of a dental device 100 according to some embodiments. In some embodiments, the dental device 100 can be a bruxism treatment device. As shown, dental device 100 comprises a curved portion 110, and first and second back portions 120. In some embodiments, the dental device 100 is symmetric across a plane extending through the mid-point of the curved portion 110 and between the first and second back portions 120. In addition, first and second back portions 120 are connected to curved portion 110 by connection beams 130. In some embodiments, each of the first and second back portions 120 are connected to a unique one of the ends of the curved portion 110, and in some embodiments, each of the first and second back portions 120 is connected to a unique one of the ends of the curved portion 110 via a unique one of the connection beams 130. In some embodiments, this connection between the first and second back portions 120 and unique ends of the curved portion 110 can give the dental device 100 a U-shape, with the curved portion 110 forming the base of the U and the first and second back portions 120 forming the arms of the U.

The back portions 120 can comprise a variety of shapes and sizes. In some embodiments, the back portions 120 can comprise substantially planar members that are sized to fit comfortably between the teeth and the gums, and in some embodiments, between the teeth, gums, and cheeks of the user.

In some embodiments, the curved portion 110 and the connection beams 130 are sized and shaped such that the back portions 120 are offset from the curved portion 110. In some embodiments, each of the first and second back portions 120 are connected to the curved portion 110 by a pair of connection beams 130 and an opening 140 is formed between each of the adjacent pairs of connection beams 130. Advantageously, this opening 140 can facilitate flow of saliva in the mouth of a user and can thereby improve user comfort and decrease negative indications such as dry mouth. As further seen in FIG. 1, projections 150, respectively, extend from either of the first and second back portions 120.

The dental device 100 can comprise a variety of shapes and sizes and can be made from a variety of materials. In some embodiments, dental device 100 is a one-piece molded device formed with a flexible and resilient plastic such as a thermoplastic elastomer, for example DuPont's Elvaloy™, PVC, silicones, and other plastics and polymers. Desired softness-toughness and resilient cushion characteristics may be achieved, for example, with material of Durometer index 00-A on the Shore scale. In some embodiments, the dental device 100 is formed with a laminate having a soft surface and a tougher inner layer.

The curved portion 110 can comprise a variety of shapes and sizes. In some embodiments, the curved portion 110 is curved to generally match the curvature of a person's teeth and is sized to comfortably fit between the front teeth and gums of the person. In some embodiments, the curved portion 110, the connection beams 130, and the first and second back portions 120 are sufficiently pliable to effectively conform and fit to jaws of different sizes and curvatures.

In some embodiments, a user places the dental device 100 into their mouth, such that the curved portion 110, the connection beams 130, and the first and second back portions 120 extend along and around surfaces of the gums and teeth facing out of the mouth. In addition, in this embodiment, when in place, the projections 150 extend from the first and second back portions 120 toward the interior of the mouth, such that the projections 150 are between upper and lower teeth.

In alternative embodiments, a user may place a dental device into their mouth, such that a curved portion, connection beams, and first and second back portions of the dental device extend along surfaces of the gums and teeth facing the interior of the mouth. In addition, in this embodiment, projections of the dental device extend from first and second back portions toward the exterior of the mouth, such that the projections are between upper and lower teeth.

In some embodiments, the user places the dental device 100 into their mouth such that the curved portion 110, the connection beams 130, and the first and second back portions 120 extend along and around surfaces of the upper gums and teeth. Alternatively, in some embodiments, the user places the dental device 100 into their mouth such that the curved portion 110, the connection beams 130, and the first and second back portions 120 extend along and around surfaces of the lower gums and teeth.

The projections 150 can comprise a variety of shapes and sizes. In some embodiments, there can be any desired number of projections of each of the first and second back portions 120. In one embodiment, for example 1, 2, 3, 4, 5, 6, 7, 8, 9, 10, 15, 20, or any other or intermediate number of projections 150 can extend from the first and second back portions 120. In some embodiments, the projections 150 are compressible and cushion compressive forces between upper and lower teeth with a resistive force and return to their uncompressed state once the compressive forces are removed. Compression, deflection, and/or deformation of the projections 150 may occur in response to the compressive forces. The compression, deflection, and/or deformation of the projections 150 occurs because of, for example, the properties of the materials from which the projections 150 are made and because of the geometry of the projections. In some embodiments, plastic deformation occurs, such that the projections 150 are reshaped so as to conform to the topology of the user's teeth. In alternative embodiments, plastic deformation does not occur, such that the projections 150 only temporarily deform and return to their original shape when the compressive forces are removed.

In the embodiment shown in FIG. 1, three projections 150 extend from each of the first and second back portions 120. In some embodiments, 2 or more, 3 or more, 4 or more, 5 or more, 6 or more, 10 or more, or any other or intermediate number of projections 150 extend from each of the first and second back portions 120. In some embodiments, each projection is formed by an elongate filament or fiber, and an array of projections 150 extend from each of the first and second back portions 120. For example, an array of projections 150 some of which having a diameter or thickness of about 1 mm, 2 mm, 3 mm, 4 mm, 5 mm, 7 mm, 10 mm, 15 mm, and/or any other or intermediate value and by a length of about 1 mm, 2 mm, 3 mm, 4 mm, 5 mm, 7 mm, 10 mm, 15 mm, 20 mm, 25 mm, 30 mm, 50 mm, and/or any other or intermediate length may extend from each of the first and second back portions 120. Different sizes may alternatively be used.

In the embodiment shown in FIG. 1, the projections 150 are substantially cylindrical. In alternative embodiments, cross sections of the projections taken substantially perpendicular to the general direction of the projections have shapes other than circles. For example, such cross-sections may have a shape which is substantially rectangular, oval, polygonal, or which is irregular. In some embodiments, the projections 150 are tapered, such that the cross-sections of the projections 150 proximate the first and second back portions 120 are larger than the cross-sections of the projections 150 distal the first and second back portions 120. In some embodiments, each of the projections 150 can comprise a centerline. In some embodiments, the centerline can extend from a point of intersection between the projection 150 and the respective one of the first and second back portions 120, and to the end of the projection 150. In some embodiments, the centerline of some or all of the projections 150 can be offset from a centerline of the curved portion 110. In some embodiments, the centerline of some or all of the projections 150 can be perpendicular to the face of the respective one of the first and second back portions 120 with which the projection 150 connects.

The projections 150 of the embodiment shown in FIG. 1 have different sizes. In alternative embodiments, the projections are substantially the same size.

The projections 150 of the embodiment shown in FIG. 1 are tubular. In some embodiments, the first and second back portions 120 also include holes 160 which are aligned with the projections 150 extending therefrom. Accordingly, in such embodiments, a plurality of cavities, each extending through the first or second back portion 120 and through one of the projections 150, forms a passageway, for example, for saliva. In alternative embodiments, the projections are not tubular.

In some embodiments, tubular projections 150 can have better cushioning and durability than other projection shapes. In some embodiments, for example, a tubular projection 150 can allow for deformation of the tube when a compressive force is applied. Thus, the tubular shape of the projection 150 provides a range of resistances as the tubular projection 150 is deformed. This range of resistances can provide increased cushioning which increases the effectiveness of the dental device 100 and increases user comfort when using the dental device 100. Further, a cylindrical shaped projections 150, and specifically, a tubular shaped projection can provide cushioning and resistance to torsional forces that may be applied, for example, when the user grinds his teeth. In some an embodiment, the tubular shape of the projections 150 allows for the twisting of the projections 150 when torsional forces are applied to the projections 150. In some embodiments, can enable the projections 150 to withstand motions and forces associated with teeth grinding without sustaining damage. In some alternate embodiments, the projections 150 are solid, and include no passageway therethrough.

In the embodiment of FIG. 1, back portions 120 are each connected with front portion 110 by two connection beams 130, which two connection beams 130 are spaced apart to form an opening through which, for example, saliva may flow. In alternative embodiments, back portions 120 are each connected with front portion 110 by three or more connection beams 130. In such embodiments, adjacent beams may be spaced apart to form multiple openings.

Figure 2:
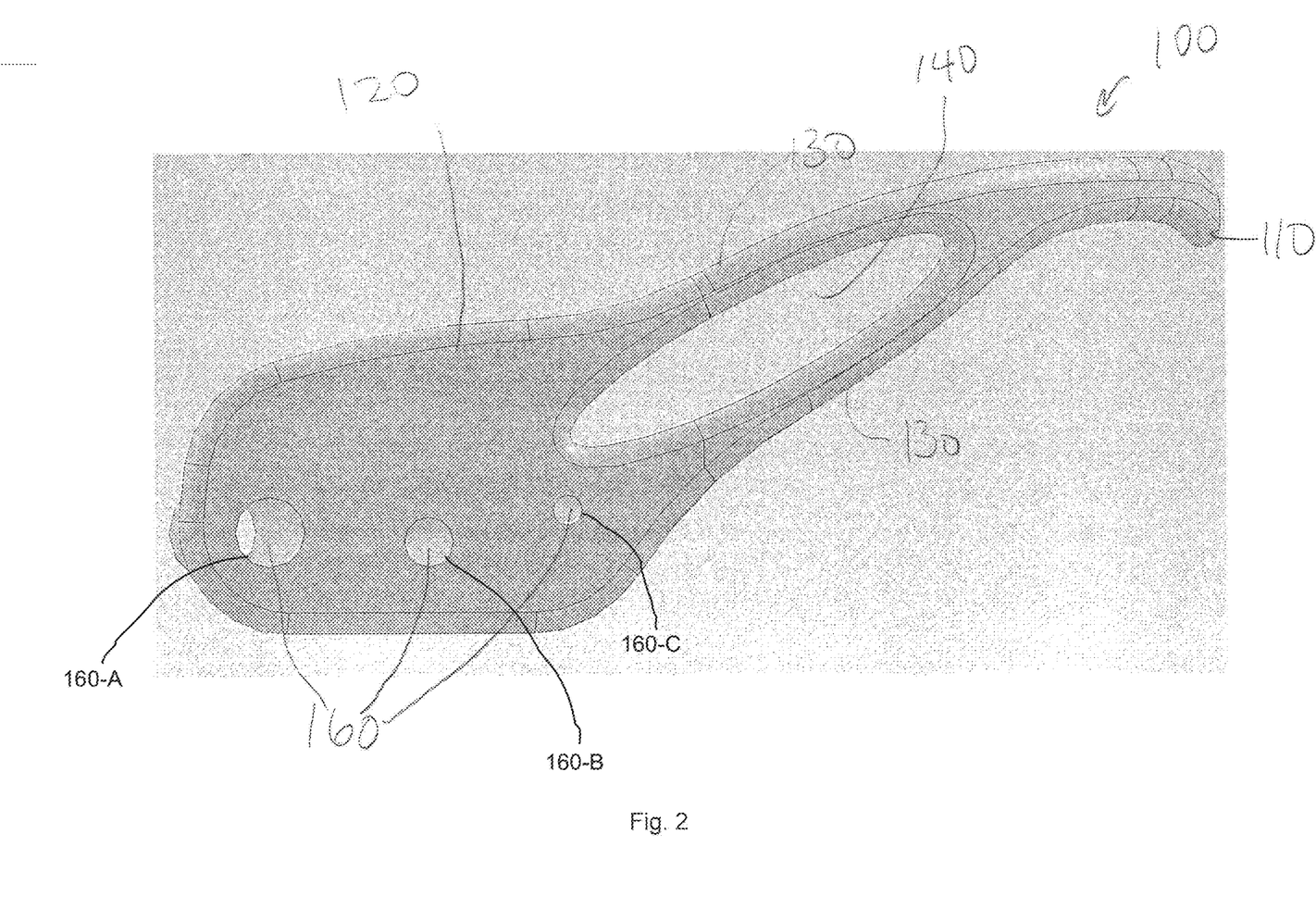
FIG. 2 is a side view of one embodiment of the bruxism treatment device.

FIG. 2 is a side view of one embodiment of the dental device 100. As shown, the back portion 120 is connected to the curved portion 110 by the connection beams 130, and an opening 140 is formed between the connection beams 130. Furthermore, the back portion 120 includes holes 160, which are aligned with tubular projections, and through which the tubular projections can be seen in the illustrated perspective. As specifically seen in FIG. 2, the back portion 120 can include a first hole 160-A, a second hole 160-B, and a third hole 160-C.

As shown in FIG. 2, the holes 160 and corresponding projections have different sizes. Specifically, as is shown in the embodiment, the first hole 160-A has the largest diameter, and the third hole 160-C has the smallest diameter.

In addition, the holes 160 are arranged nonlinearly, such that their centers do not align. Furthermore, there is no line which is tangent to all of the holes 160. It therefore follows that the projections 150 are also arranged nonlinearly, such that their centers do not align, and such that there is no line which is tangent to all of the projections. Advantageously, the non-linear arrangement of the holes 160, and also of the projections 150, can increase the size of the range through which cushioning can be provided to a user when the dental device 100 is in use. Advantageously, this increase in the size of the range through which cushioning can be provided can increase the performance of the dental device 100 and increase user comfort when using the dental device.

Similarly, a plane defined as passing through the longitudinal, central axes of any two of the holes 160 and/or projections 150 shown in FIG. 2, would not pass through the longitudinal, central axis of the third hole 160 and/or third projection 150. In the embodiment depicted in FIG. 2, the plane defined by the longitudinal, central axes of holes 160-A and 160-B passes below the longitudinal, central axis of hole 160-C. Thus, the holes 160 and/or the projections 160 are non-coplanar.

Figure 3:
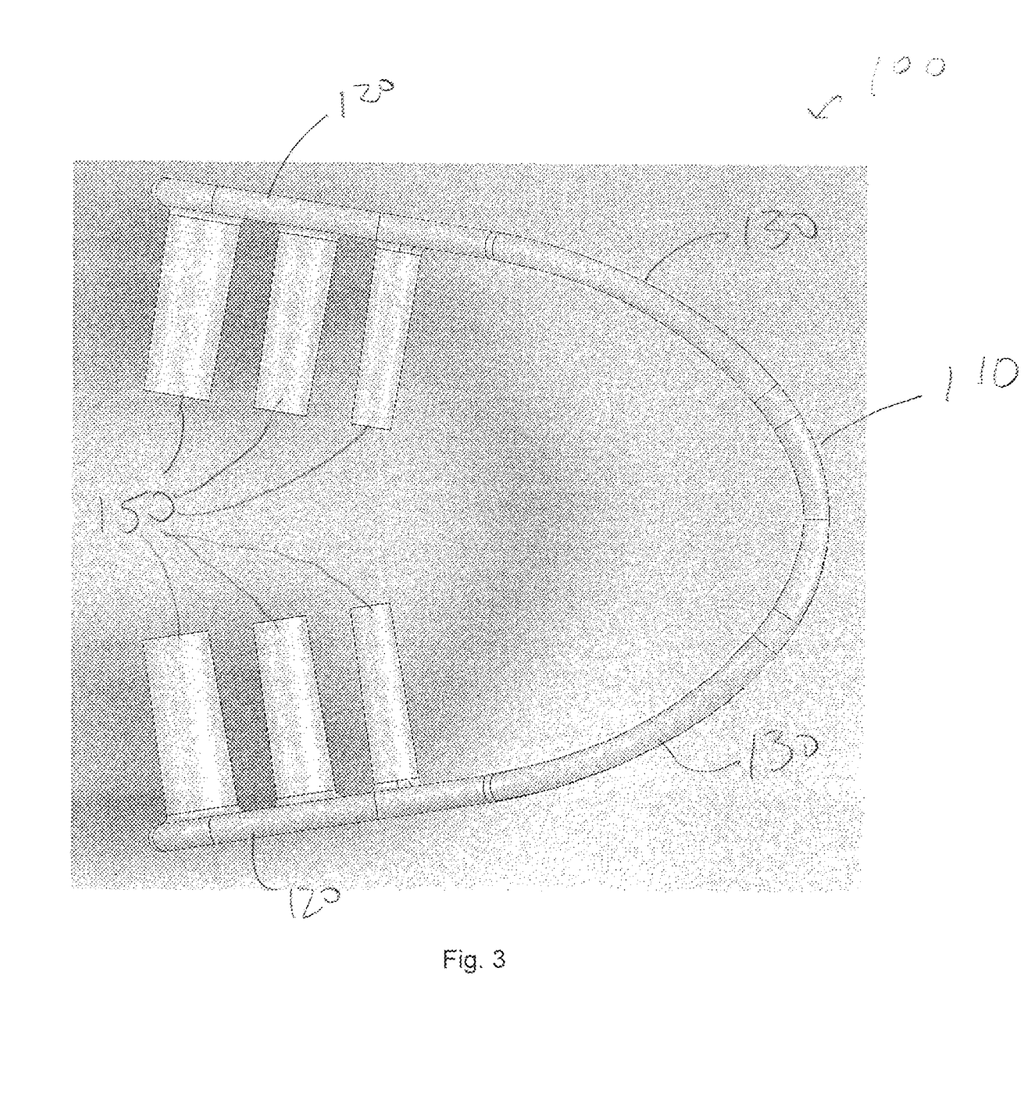
FIG. 3 is a top view of one embodiment of the bruxism treatment device.

FIG. 3 is a top view of one embodiment of the dental device 100. As shown, the first and second back portions 120 are connected to the curved portion 110 by the connection beams 130. Furthermore, the projections 150, respectively, extend from either of the first and second back portions 120. As shown in FIG. 3, the projections 150 have different sizes, and are tapered.

Figure 4:
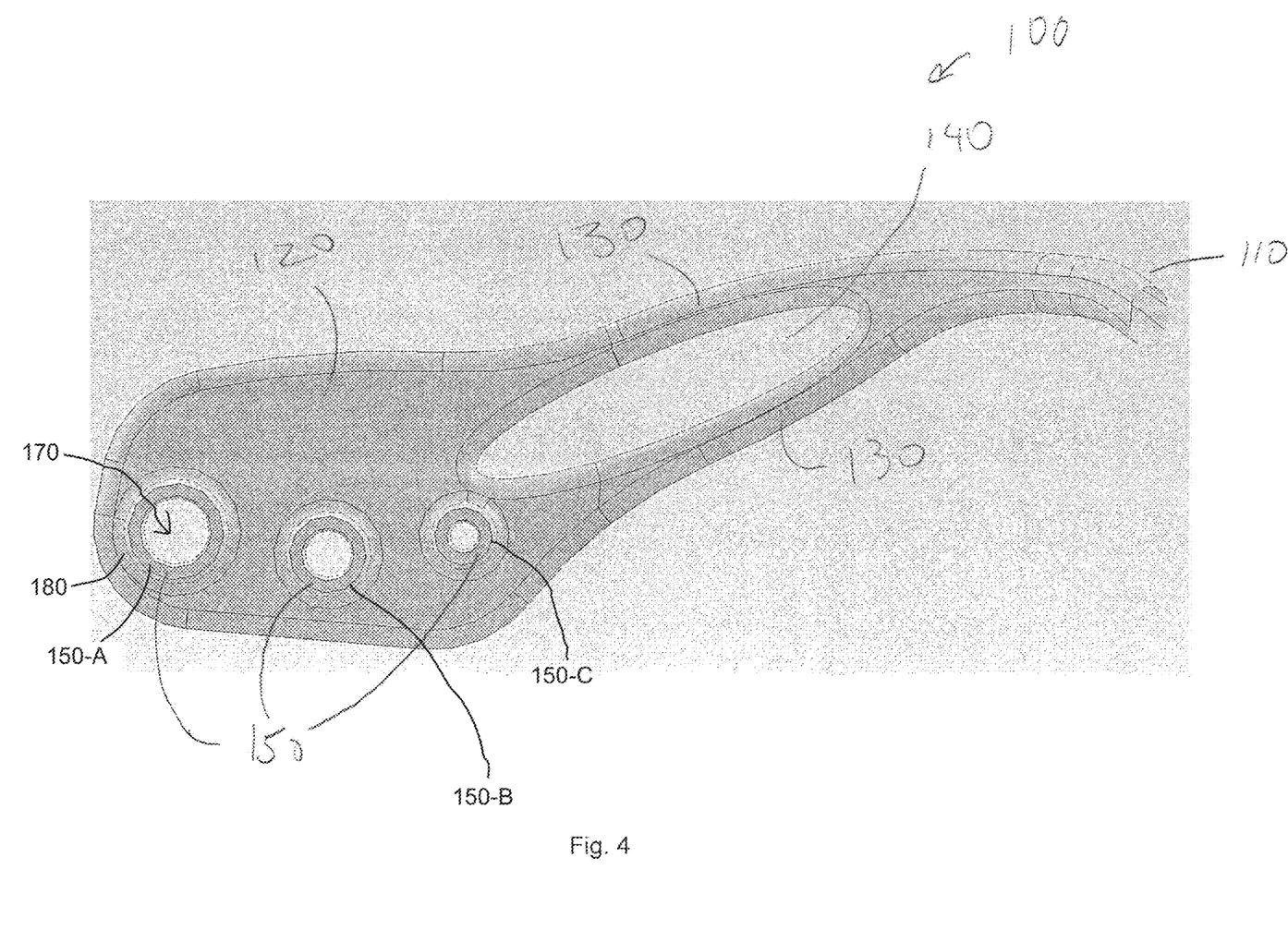
FIG. 4 is a section view of one embodiment of the bruxism treatment device.

FIG. 4 is a side, section view of one embodiment of the dental device 100. As shown, the back portion 120 is connected to the curved portion 110 by the connection beams 130, and an opening 140 is formed between the connection beams 130. Furthermore, the tubular projections 150 extend from the back portion 120. As seen in FIG. 4, the projections 150 can comprise a lumen 170 defined in part by walls 180 of the projection 150. The walls 180 can be any desired thickness. In some embodiments, the walls 180 can have a thickness of 0.1 mm, 0.2 mm, 0.3 mm, 0.4 mm, 0.5 mm, 1 mm, 2 mm, 3 mm, 5 mm, 10 mm, and/or any other or intermediate thickness. In some embodiments, the thickness of the walls 180 can influence the degree of cushioning provided by the projections 150.

As shown in FIG. 4, the dental device 100 has cavities which extend both through the projections 150 and through the back portion 120. As also shown in FIG. 4, the projections have cross-sectional shapes which are polygonal. As specifically seen in FIG. 4, the back portion 120 can include a first projection 150-A, a second projection 150-B, and a third projection 150-C.

As shown, the projections 150-A, 150-B, 150-C have different sizes. Specifically, as is shown in the embodiment, the first projection 150-A, which projection is relatively farthest from the curved portion 110, has the largest diameter, and the third hole 150-C, which is relatively closest to the curved portion 110, has the smallest diameter. Advantageously, providing the first projection 150-A with the largest diameter can increase the amount of cushioning experienced at the back of the mouth, where the largest bite-forces are experienced.

As shown in FIG. 4, the holes 160 and corresponding projections have different sizes. In addition, the holes 160 are arranged nonlinearly, such that their centers do not align. Furthermore, there is no line which is tangent to all of the holes 160. It therefore follows that the projections are also arranged nonlinearly, such that their centers do not align, and such that there is no line which is tangent to all of the projections.

Figure 5:
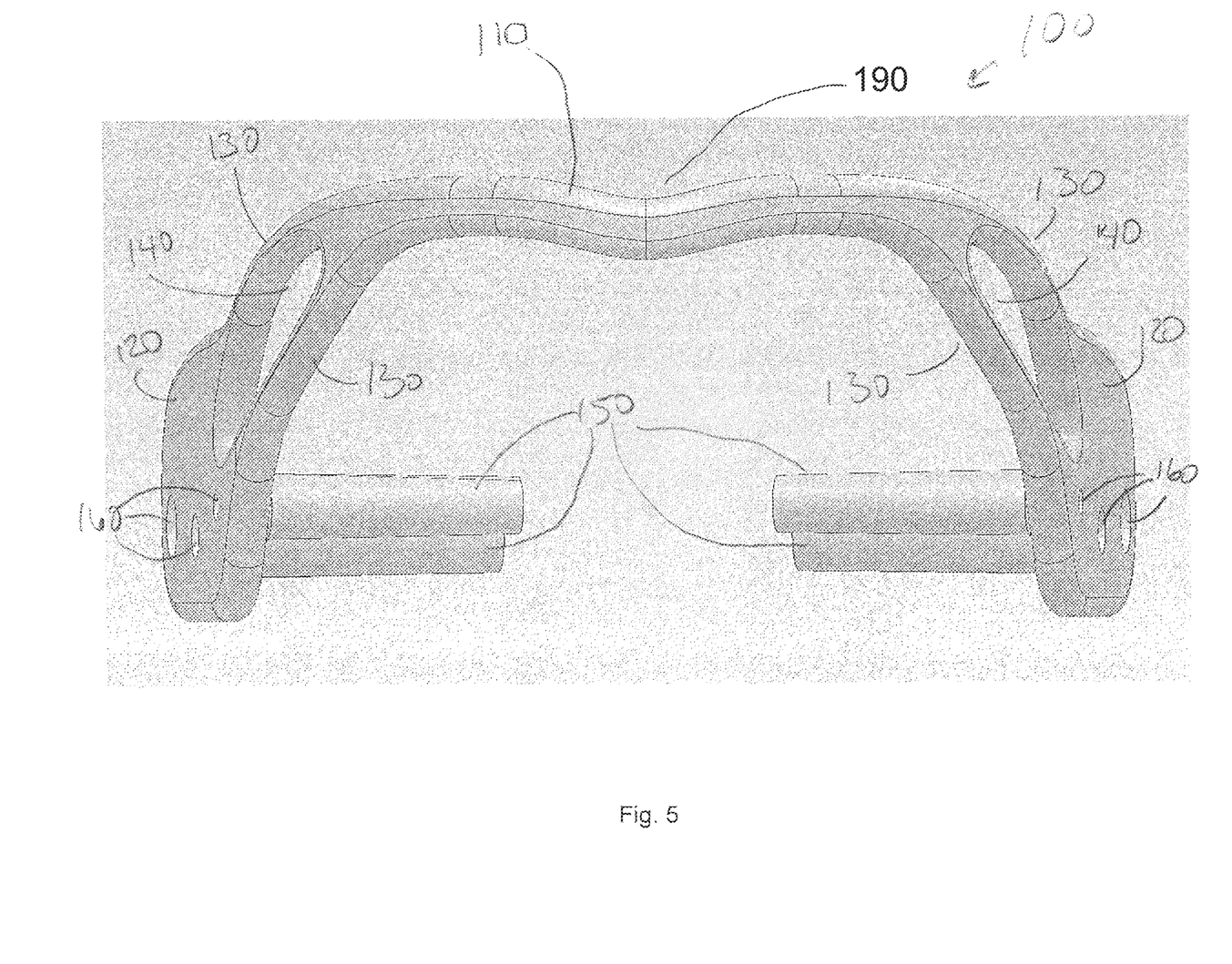
FIG. 5 is a front view of one embodiment of a bruxism treatment device.

FIG. 5 is a front view of one embodiment of the dental device 100. As seen in FIG. 5, the first and second back portions 120 are connected to the curved portion 110 by the connection beams 130, and an opening 140 is formed between adjacent pairs of the connection beams 130. Furthermore, the projections 150, respectively, extend from either of the first and second back portions 120, and the back portions 120 include the holes 160, which are aligned with the projections 150.

As shown in FIG. 5, at the center of the curved portion 110 is a recess 190 formed by a bend in the curved portion 110. The recess 190 is configured to substantially align with, but not contact or rub against the user's upper or lower lip frenulum.

While various embodiments of present invention have been described, it will be apparent to those of skill in the art that many more embodiments and implementations are possible that are within the scope of this invention. Accordingly, the present invention is not to be limited to the described embodiments.

What is claimed is:

1. A dental device comprising:
   a curved portion;
   first and second back portions connected to the curved portion; and
   projections configured to be positioned between occlusal surfaces of teeth of a patient, the projections comprising:
      at least three first cylindrical projections extending from the first back portion, wherein each of the projections in the at least three first cylindrical projections defines a centerline, wherein the centerline of one of the at least three first cylindrical projections is non-coplanar with a plane defined by the centerlines of others of the at least three first cylindrical projections;
      at least three second cylindrical projections extending from the second back portion, wherein each of the projections in the at least three second cylindrical projections defines a centerline, wherein the centerline of one of the at least three second cylindrical projections is non-coplanar with a plane defined by the centerlines of others of the at least three second cylindrical projections;
   wherein each of the projections is tubular, wherein each centerline of the at least three first cylindrical projections extends from the first back portion towards a respective second cylindrical projection.

2. The dental device of claim 1, wherein the at least three first and second cylindrical projections comprise tapered cylindrical projections.

3. The dental device of claim 2, wherein at least one of the projections on each of the first and second back portions comprises an enlarged diameter.

4. The dental device of claim 3, wherein the at least one of the projections comprising the enlarged diameter is positioned relatively farther from the curved portion than the others of the projections on each of the first and second back portions.

5. The dental device of claim 2, wherein the at least three first and second cylindrical projections are only connected by the one of the first and second back portions from which the at least three first and second cylindrical projections extend.

6. The dental device of claim 1, wherein the first and second back portions comprise substantially planar members.

7. The dental device of claim 6, wherein the centerlines of the projections are perpendicular to the one of the first and second back portions with which the projections connect.

8. The dental device of claim 1, wherein the first and second back portions are connected to the curved portion via a pair of beam members, wherein the beam members define an opening configured to allow passage of saliva.

9. The dental device of claim 8, wherein the at least three first and second cylindrical projections are plastically deformable when compressed.

10. An intraoral device, comprising:
a curved portion configured to extend along a user's teeth;
first and second back portions connected to the curved portion; and
a plurality of non-coplanar cylindrical projections extending from each of the first and second back portions, wherein each of the projections is tubular, wherein the projections are only connected to each other by the one of the first and second back portions from which the projections extend, wherein the projections are positioned such that, when in the user's mouth, the projections engage occlusal surfaces of upper and lower teeth of the user, the plurality of non-coplanar cylindrical projections comprising:
at least three first cylindrical projections extending from the first back portion, wherein a centerline of one of the at least three first projections is non-coplanar with a plane defined by the centerlines of others of the at least three first projections; and
at least three second cylindrical projections extending from the second back portion, wherein a centerline of one of the at least three second projections is non-coplanar with a plane defined by centerlines the others of the at least three second projections, wherein each centerline of the at least three first cylindrical projections extends from the first back portion towards a respective second cylindrical projection.

11. The device of claim 10, wherein the first and second back portions are connected to the curved portion by a plurality of beams.

12. The device of claim 11, wherein the plurality of beams comprise a first pair of adjacent beams connecting the first back portion to the curved portion, and wherein the plurality of beams comprises a second pair of adjacent beams connecting the second back portion to the curved portion.

13. The device of claim 12, further comprising a first opening between the first pair of adjacent beams and a second opening between the second pair of adjacent beams.

14. The device of claim 10, wherein one or more of the first and second back portions comprises one or more holes, each aligned with one of the projections.

15. The device of claim 10, wherein the projections have differing sizes.

16. The device of claim 10, wherein one or more of the projections is tapered so as to be larger proximate the first and second back portions and smaller distal the first and second back portions.

17. A method of minimizing tooth abrasion comprising:
inserting a dental device into a mouth, wherein the dental device comprises:
a curved portion;
first and second back portions connected to the curved portion; and
projections comprising:
at least three first cylindrical projections extending from the first back portion, wherein each of the projections in the at least three first cylindrical projections defines a centerline, wherein the centerline of one of the at least three first cylindrical projections is non-coplanar with a plane defined by the centerlines of others of the at least three first cylindrical projections;
at least three second cylindrical projections extending from the second back portion, wherein each of the projections in the at least three second cylindrical projections defines a centerline, wherein the centerline of one of the at least three second cylindrical projections is non-coplanar with a plane defined by the centerlines of others of the at least three second cylindrical projections; wherein each centerline of the at least three first cylindrical projections extends from the first back portion towards a respective second cylindrical projection, and wherein each of the cylindrical projections is tubular; and
positioning the dental device such that the at least three first and second cylindrical projections extending from each of the first and back portions engage occlusal surfaces of upper and lower teeth.

18. The method of minimizing tooth abrasion of claim 17, wherein at least one of the projections on each of the first and second back portions comprises an enlarged diameter.

19. The method of minimizing tooth abrasion of claim 18, wherein the at least one of the projections comprising the enlarged diameter is positioned relatively farther from the curved portion than the others of the projections on each of the first and second back portions.

20. The method of minimizing tooth abrasion of claim 17, wherein the first and second back portions comprise substantially planar members.

21. The method of minimizing tooth abrasion of claim 20, wherein the centerlines of the projections are perpendicular to the one of the first and second back portions with which the projections connect.

22. The method of minimizing tooth abrasion of claim 17, wherein the first and second back portions are connected to the curved portion via a pair of beam members.

23. The method of minimizing tooth abrasion of claim 22, wherein the beam members define an opening configured to allow passage of saliva.

24. The method of minimizing tooth abrasion of claim 17, wherein the at least three first and second cylindrical projections are tapered.

\* \* \* \* \*